US006881725B2

(12) United States Patent
Yerxa et al.

(10) Patent No.: US 6,881,725 B2
(45) Date of Patent: Apr. 19, 2005

(54) METHOD FOR TREATING PAIN

(75) Inventors: Benjamin R. Yerxa, Raleigh, NC (US); Ward M. Peterson, Morrisville, NC (US); Christopher S. Crean, Apex, NC (US)

(73) Assignee: Inspire Pharmaceuticals Inc., Durham, NC (US)

( * ) Notice: Subject to any disclaimer, the term of this patent is extended or adjusted under 35 U.S.C. 154(b) by 21 days.

(21) Appl. No.: 10/355,699

(22) Filed: Jan. 31, 2003

(65) Prior Publication Data

US 2003/0158147 A1 Aug. 21, 2003

Related U.S. Application Data

(60) Provisional application No. 60/353,213, filed on Feb. 1, 2002.

(51) Int. Cl.[7] .................. C07H 21/00; A61K 31/70
(52) U.S. Cl. .................. 514/47; 514/12; 514/51; 514/277; 514/851; 536/26.1; 536/25.6; 424/45; 424/427; 128/898; 623/4.1; 606/107
(58) Field of Search .................. 514/12, 47, 51, 514/851, 277, 48, 50; 536/25.6, 26.1, 26.23; 424/45, 427, 46; 128/898; 623/4.1; 606/107

(56) References Cited

U.S. PATENT DOCUMENTS 6,462,028 B1 * 10/2002 Pendergast et al. ............ 514/47

FOREIGN PATENT DOCUMENTS

| JP | 10059990 | 3/1998 |
|----|----------|--------|
| WO | WO 98/03177 | 1/1998 |
| WO | WO 00/30629 | 6/2000 |
| WO | WO 01/45691 | 6/2001 |
| WO | WO 02/16381 | 2/2002 |
| WO | WO 03/000056 | 1/2003 |

OTHER PUBLICATIONS

Chizh et al "P2X receptors and nociception.", Pharmacol. Rev. 53(4): 553–568,2000.*
Burnstock, "Physiological and Pathological Roles of Purines: An Update," Drug Dev. Res. 28:195–206 (1993).
Chizh and Illes, "P2X Receptors and Nociception," Pharmacol. Rev. 53(4):553–568 (2000).
Collier et al., "The Adcominal Constriction Response and its Suppression by Analgesic Drugs in the Mouse," Br. J. Pharmac. Chemother. 32:295–310 (1968).
Goodman & Gilman, The Pharmacologic Basis of Therapeutics, McGraw–Hill, p. 529 (1996).
Holton and Holton, "The capillary Dilator Substances in Dry Powders of Spinal Roots; a Possible Role of Aensoine Triphosphate in Chemical Transmission from Nerve Endings," J. Physiol. (Lond.) 126:124–140 (1954).
Jarvis and Kowaluk, "Pharmacological Characterization of P2X$_3$ Homomeric and Heteromeric Channels in Nociceptive Signaling and Behavior," Drug Development Res. 52:220–231 (2001).

(Continued)

Primary Examiner—James O. Wilson
Assistant Examiner—Devesh Khare
(74) Attorney, Agent, or Firm—Howrey Simon Arnold & White, LLP; Viola T. Kung

(57) ABSTRACT

The present invention is directed to a method of treating pain. The method comprises administering to a subject a pharmaceutical composition comprising an effective amount of a P2X receptor antagonist. The methods of the present invention are useful in reducing pain, such as traumatic pain, neuropathic pain, organ pain and pain associated with diseases. The P2X receptor antagonists particularly useful for this invention are mononucleoside polyphosphate derivatives or dinucleoside polyphosphate derivatives of general Formula I. The compounds of the present method can be used alone to treat pain. The compounds of the present method can also be used in conjunction with other therapeutic agents or adjunctive therapies commonly used to treat pain, thus enhancing the overall pain-reducing effect in a subject in need of such treatment.

26 Claims, 5 Drawing Sheets

OTHER PUBLICATIONS

Kim and Chung, "An experiemental model for peripheral neuropathy produced by segmental spinal nerve ligation in the rat," *Pain* 50:355–363 (1992).

Lewis et al., "Coexpression of $P2X_2$ and $P2X_3$ receptor subunits can account for ATP–gated currents in sensory neurons," *Nature* 377:432–435 (1995).

Maciewicz and Martin, *Harrison's Principles of Internal Medicine, 12th Edition*, Jean D. Wilson et al., editors, McGraw–Hill, Inc., New York, p. 93 (1991).

Zhong, et al. "Pharmacological and molecular characterization of P2X reeptors in rat pelvic ganglion neurons," *Br. J. Pharmacol.* 125:771–781 (1998).

Burnstock, et al., "P2 Purinergic Receptors: Modulation of Cell Function and Therapeutic Potential," *Journal of Pharmacology and Experimental Therapeutics* 295(3):862–869 (2000).

Ding, et al., "ATP, P2X receptors and pain pathways," *Journal of Automatic Nervous System* 81:289–294 (2000).

European Search Report, issued Sep. 11, 2003.

Zatorski, et al., "Chemical Synthesis of Benzamide Adenine Dinucleotide: Inhibition of Inosine Monophosphate Dehydrogenase (Types I and II)," *J. Med. Chem.* 39:2422–2426 (1996).

* cited by examiner

METHOD FOR TREATING PAIN

This application claims the benefit of U.S. Provisional Application No. 60/353,213, filed Feb. 1, 2002.

TECHNICAL FIELD

This invention relates to a method of treating pain and pharmaceutical compositions of use in the treatment of pain, such as traumatic pain, neuropathic pain, organ or tissue pain, and pain associated with diseases. More particularly, the present invention relates to a method of decreasing or preventing pain associated with diseases, trauma or other conditions by administering pharmaceutical compositions of the present invention.

BACKGROUND OF THE INVENTION

The general term "pain" is defined here to represent all categories of physical pain. This includes traumatic pain resulting from injury, surgery or inflammation. It also includes pain associated with diseases such as cancer, AIDS, arthritis, and herpes. Pain associated with neuropathy such as diabetic neuropathy, causalgia, brachial plexus avulsion, occipital neuralgia, fibromyalgia, vulvodynia, prostadynia, pelvic pain, gout, and other forms of neuralgia, such as neuropathic and idiopathic pain syndromes are also included. Specific organ- or site-localized pain, such as headache, ocular and corneal pain, bone pain, urogenital pain, heart pain, skin/burn pain, lung pain, visceral (kidney, gall bladder, etc.) pain, joint pain, dental pain and muscle pain are further included in this invention. The general term "pain" also covers pain symptoms of varying severity, i.e. mild, moderate and severe pain, as well as those of acute and chronic pain.

Traumatic or nociceptive pain differs from neuropathic pain in that an external stimulus causes a normal sensory response to an insult or illness in the case of traumatic pain, whereas neuropathic pain results from injury to a portion of the nervous system and is typically not responsive to narcotic analgesics. Neuropathic pain often involves neural hypersensitivity and can persist without any overt external stimulus. (Goodman & Gilman's "The Pharmacologic Basis of Therapeutics", 1996, p. 529, McGraw-Hill).

The therapeutic objective of most pain therapy is to alleviate the symptoms of pain regardless of the cause. Current pain-control therapies include the use of opioid narcotic analgesics such as morphine and fentanyl, nonsteroidal anti-inflammatory drugs (NSAIDS) such as aspirin, ibuprofen and cyclooxygenase inhibitors, or ion channel blockers such as lidocaine and novocaine. These therapies all have limitations, however. Opioids can cause tolerance, dependence, constipation, respiratory depression and sedation. NSAIDS have gastrointestinal side effects, can increase bleeding time, and are not effective in the treatment of severe pain. In the case of non-selective sodium channel blockers, central nervous system (CNS) side effects, cardiovascular side effects and corneal damage have been reported after use. Given the above limitations to currently known pain-control therapies, a need still exists for better pain-treatment methods.

Purine derivatives, acting via extracellular nucleotide receptors, have a variety of physiological and pathological roles in living tissues and cell types (Burnstock, *Drug Dev. Res.* 28:195–206 (1993)). Extracellular nucleotide receptors have been studied in a number of neurons from afferent and efferent nerve fibers including sensory, sympathetic, parasympathetic, mesenteric, and central neurons (Zhong, et al. *Br. J. Pharmacol.* 125:771–781 (1998)), and purines, such as ATP, function as excitatory neurotransmitters. These compounds are known to activate P2X receptors located on primary afferent nerve fibers and tissues of the spinal cord dorsal horn (Holton and Holton, *J. Physiol.* (Lond.) 126:124–140 (1954)). Neurons that process nociceptive information are also found in the spinal cord dorsal horn (Maciewicz, R. and Martin, J. B. in Harrison's Principles of Internal Medicine, 12$^{th}$ Edition, McGraw-Hill, Inc., New York, Jean D. Wilson, et al., editors, 1991, P.93).

Nucleotide receptors, in particular, P2X receptors, are known to form homomultimers or heteromultimers in vitro. Two of the receptors/subunits from the P2X family, $P2X_2$ and $P2X_3$, can form functional ATP-gated channels when expressed alone or when co-expressed in a heteromultimer form ($P2X_{2/3}$). These heteromultimers produce ion currents which are similar to currents seen in native sensory channels (Lewis, et. al, *Nature* 377:432–435 (1995)). Furthermore, nociception has been documented to occur via stimulation of these P2X receptors (in particular within the previously described $P2X_2$, $P2X_3$ and $P2X_{2/3}$ receptor types), and activation of these P2X receptors with agonists such as ATP or benzoylbenzoyl-ATP is associated with hyperalgesic action (Chizh and Illes, *Pharmacol. Rev.* 53:553–568 (2000); Jarvis and Kowaluk, *Drug Development Res.* 52:220–231 (2001)). A contrasting example of the causal relationship between antagonism of these P2X receptors and antinociception is provided by the ATP-ketal derivative, TNP-ATP, which has been shown to produce antinociceptive effects in rats (Jarvis and Kowaluk, 2001). Substances previously shown to antagonize these P2X receptors (such as TNP-ATP), however, are generally known to have thermal instability and/or receptor selectivity problems; hence they are poor candidates for pharmaceutical development. The need still exists for new pain treatment methods based on materials with good receptor selectivity, chemical stability and low incidences of side effects.

As described above, agents commonly used to treat pain may cause adverse side effects, and thus there is a continuing need for new agents that are both safe and effective in treating pain.

SUMMARY OF THE INVENTION

The present invention is directed to a method of treating, reducing, or preventing pain. The present invention preferably comprises a method of treating, reducing, or preventing pain associated with traumatic pain, neuropathic pain, inflammatory pain, acute pain, chronic pain, organ or tissue pain, and pain associated with diseases. The method comprises administering to a subject a pharmaceutical composition comprising a therapeutically effective amount of a nucleotide receptor modulator. The nucleotide receptor modulator is preferably a pharmaceutical composition comprising an effective amount of a P2X receptor antagonist. The P2X receptor is preferably a P2X receptor complex comprising at least one $P2X_3$ subunit.

The P2X receptor antagonists particularly useful for this invention are mononucleoside polyphosphate derivatives or dinucleoside polyphosphate derivatives. In one embodiment, the P2X receptor antagonists useful for this invention are mononucleoside polyphosphate derivatives or dinucleoside polyphosphate derivatives of general Formula I.

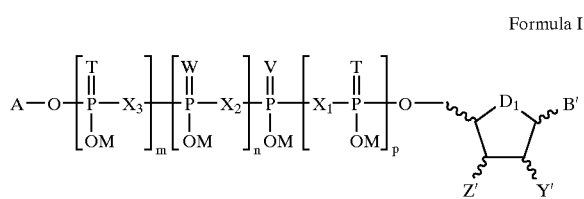

Formula I

One embodiment of the present invention relates to pharmaceutical compositions comprising a therapeutically effective amount of a compound of Formula I or a pharmaceutically acceptable salt, amide, or ester thereof, in combination with a pharmaceutically acceptable carrier.

The present invention relates to a method for reducing pain in a mammal in need of such treatment comprising administering a therapeutically effective amount of a compound of Formula I or a pharmaceutically acceptable salt, amide, or ester thereof in combination with a pharmaceutically acceptable carrier.

The compounds of the present invention can be used alone to treat pain. The compounds of the present invention can also be used in conjunction with other therapeutic agents or adjunctive therapies commonly used to treat pain, thus enhancing the therapeutically desired effect of pain reduction at the area or areas in need of treatment.

DETAILED DESCRIPTION OF THE INVENTION

Figure 1:
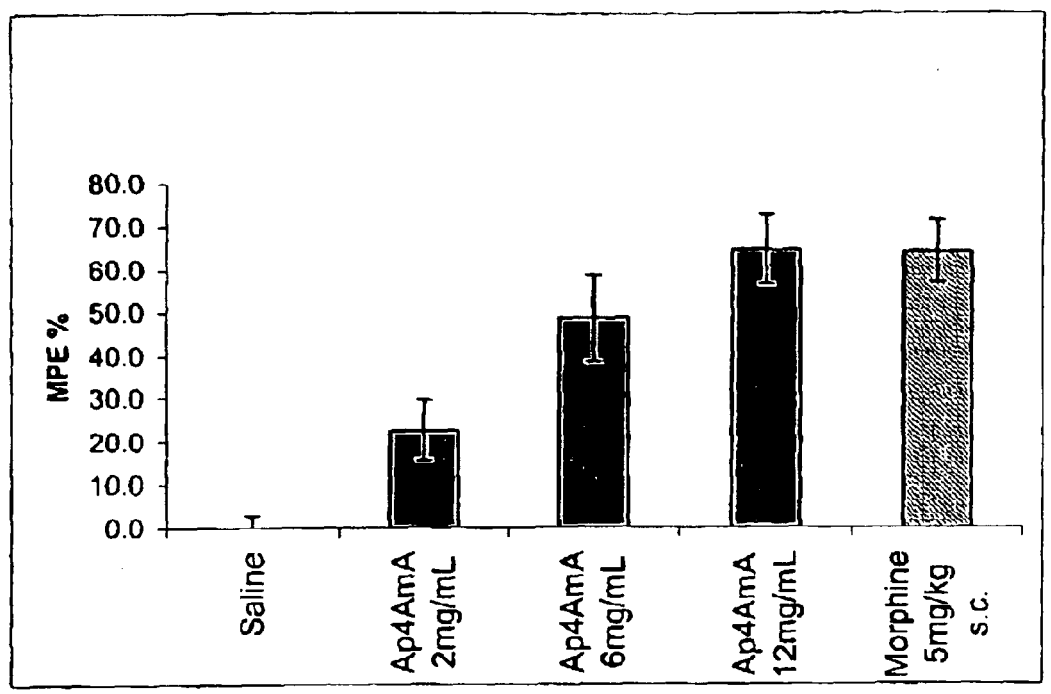
FIG. 1 shows the antinociceptive effect of administration of $AP_4AmA$ ($AP_4A$-2', 3'-monoacetal with phenylacetaldehyde) and morphine in the mouse in a preclinical model of acute nociception (the hotplate model).

The applicants have unexpectedly discovered that compounds of the present invention are useful in treating pain. As shown herein, pharmaceutical compositions containing compounds of the present invention of Formula I have utility in the attenuation of pain signaling and therefore are useful for the treatment or prevention of pain. The method of the present invention does not have many of the deficiencies and side effects of current commercial compounds and fulfills a need in treating pain by new modes or targets.

According to the present invention, the method of treating pain is in a subject in need of such treatment regardless of the cause or location of the bodily pain. The method according to a preferred embodiment of the present invention reduces pain with furanose-modified nucleoside polyphosphate derivatives and/or their dinucleotide analogs. The method comprises administering to a subject a pharmaceutical composition comprising an effective amount of a compound of Formula I (the subject is a mammal, preferably a human). The methods of the present invention are useful in the treatment of pain comprising traumatic pain, neuropathic pain, organ or tissue pain, or pain associated with diseases. An effective amount of said compound is an amount that leads to a reduction of nociception and/or ameliorates the symptoms of pain.

The method of the present invention alleviates the symptoms of pain regardless of the cause of the pain. Pain treatable by the present method includes traumatic pain, neuropathic pain, organ and tissue pain, and pain associated with diseases. Traumatic pain includes pain resulting from injury, post-surgical pain and inflammatory pain. Neuropathic pain includes neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ or tissue pain includes headache, ocular pain, corneal pain, bone pain, heart pain, skin/burn pain, lung pain, visceral pain (kidney, gall bladder, etc.), joint pain, dental pain, muscle pain, pelvic pain, and urogenital pain (e.g. vulvodynia and prostadynia). Pain associated with diseases includes pain associated with cancer, AIDS, arthritis, herpes and migraine. The present invention reduces pain of varying severity, i.e. mild, moderate and severe pain in acute and/or chronic modes.

Description of Compounds

The nucleotide and dinucleotide compounds useful for this invention include compounds of Formula I, and amides, esters, or salts thereof:

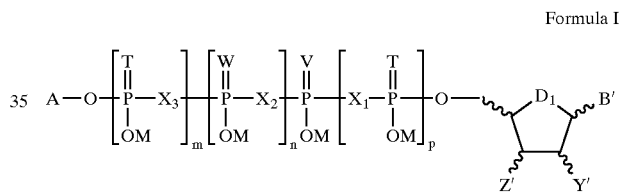

Formula I wherein:

$X_1$, $X_2$, and $X_3$ are independently oxygen, methylene, monochloromethylene, dichloromethylene, monofluoromethylene, difluoromethylene, or imido;

T, W, and V are independently oxygen or sulfur;

m=0, 1 or 2;

n=0 or 1;

p=0, 1, or 2;

where the sum of m+n+p is from 0 to 5;

each M is independently hydrogen or a pharmaceutically-acceptable inorganic or organic counterion;

A=M, or

A is a nucleoside residue which is defined as:

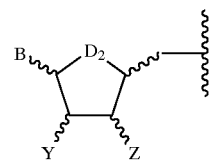

and is linked to the phosphate chain via the 5' position of the furanose or carbocycle;

Z is H, F or $OR_1$;

Z' is H, F or $OR_3$;

Y is H, F or $OR_2$;

Y' is H, F or $OR_4$;

$R_1$, $R_2$, $R_3$, and $R_4$ are independently H or a residue according to Formulas II and/or III;
provided that when A=M, at least one of Y' and Z' equals $OQ(R_5R_6R_7)$ under the definition of Formula II; or Y' and Z' taken together form a ring as defined in Formula III;
further provided that when A is a nucleoside, at least one of Y, Y', Z, or Z' equals $OQ(R_5R_6R_7)$ under the definition of Formula II; or either Y and Z taken together, or Y' and Z' taken together form a ring as defined in Formula III;
$D_1$ and $D_2$ are independently O or C;

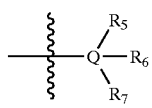

Formula II wherein:
Q is a carbon atom;
$R_5$, $R_6$, and $R_7$ are independently H, F, alkyl, cycloalkyl, aralkyl, aryl, substituted aralkyl, or heterocyclic moiety, or
$R_5$ and $R_6$, are taken together to form a carbocyclic or heterocyclic ring of 4 to 7 members, such that the moiety defined according to Formula II when attached to the oxygen is an ether; or
$R_5$ and $R_6$ are taken together as oxygen or sulfur doubly bonded to Q, and $R_7$ is alkyl, cycloalkyl, aralkyl, substituted aralkyl, aryl, or a heterocycle of 4 to 7 members, such that the moiety defined according to Formula II when attached to the oxygen is an ester or thioester; with the provision that when $R_5$ and $R_6$ are taken together as oxygen, and A=M, and $X_1$=oxygen, then $R_7$ is not benzoylbenzoyl; or
$R_5$ and $R_6$ are taken together as oxygen or sulfur doubly bonded to Q, and $R_7$ is amino or mono- or disubstituted amino, where the substituents are alkyl, cycloalkyl, aralkyl, aryl, or substituted aralkyl, or where the substituents on nitrogen form a heterocyclic ring of 4 to 7 members such that the moiety according to Formula II when attached to the oxygen is a carbamate or thiocarbamate; or
$R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II when attached to the oxygen is a carbonate or thiocarbonate;

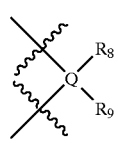

Formula III wherein $R_1$ and $R_2$ and/or $R_3$ and $R_4$ are taken together to form Q;
Q is a carbon atom;
$R_8$ and $R_9$ are taken together as oxygen or sulfur doubly bonded to Q to form a cyclical carbonate or thiocarbonate; or $R_8$ and $R_9$ can be taken together to form a ring of 4 to 7 members, with or without substituents, with or without unsaturation and with or without heteroatoms in the ring, with the provision that when A=M, and $X_1$=oxygen, said ring can have no more than two nitro groups as substituents or
$R_8$ is hydrogen, alkyl, cycloalkyl, aralkyl, substituted aralkyl, aryl, or heterocycle;

$R_9$ is hydrogen, alkyl, cycloalkyl, aralkyl, substituted aralkyl, aryl, heterocycle, alkyloxy, cycloalkyloxy, aralkyloxy, substituted aralkyloxy, aryloxy, or substituted aryloxy, such that Q is part of an acetal-, ketal- or ortho ester moiety;
B and B' are independently a purine or a pyrimidine residue according to Formulas IV or V which is linked to the sugar via the 9- or 1-position, respectively;

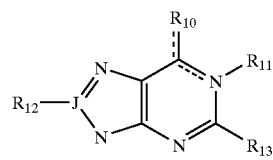

Formula IV

Formula V wherein:
$R_{10}$ and $R_{14}$ are independently hydroxy, oxo, amino, mercapto, alkylthio, alkyloxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or
$R_{10}$ and $R_{14}$ are independently acylamino, according to Formula VI; or
when $R_{10}$ or $R_{14}$ has as its first atom nitrogen, $R_{10}$ and $R_{10}$ or $R_{14}$ and $R_{15}$ are taken together to form a 5-membered fused imidazole ring (etheno compounds), optionally substituted on the imidazole ring of the etheno-compound with a substituted- or unsubstituted-alkyl, cycloalkyl, aralkyl, or aryl moiety, as described for $R_5$—$R_9$ above;
J is carbon or nitrogen, with the provision that when J is nitrogen, $R_{12}$ is not present;
$R_{11}$ is hydrogen, O(adenine 1-oxide derivatives) or is absent (adenine derivatives);
when present, $R_{12}$ is hydrogen, alkyl, azido, amino, alkylamino, arylamino or aralkylamino, hydroxy, alkoxy, aryloxy or aralkyloxy, sulfhydryl, alkylthio, arythio or aralkylthio, or $\omega$-X($C_{1-6}$alkyl)G-, wherein X is substituted- or unsubstituted-amino, mercapto, hydroxy or carboxyl and G is chosen from —O— (to give an ether), —S— (to give a thioether), —$NR_{18}$— (to give an amine), —N(CO)$R_{18}$— (to give an amide), or N(CO)OR$_{18}$— (to give a carbamate);
$R_{13}$ is hydrogen, chlorine, fluorine, hydroxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;
$R_{15}$ is hydrogen, or acyl (e.g. acetyl, benzoyl, phenylacyl, with or without substituents);
$R_{16}$ is hydrogen, alkyl (such as methyl), halo, aryl, aralkyl, alkenyl, substituted alkenyl, alkynyl, or substituted alkynyl;
preferably at least one of B or B' is a purine; more preferably at least one of B or B' is an adenine;

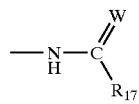

Formula VI wherein:

W is oxygen or sulfur;

$R_{17}$ is amino or mono- or disubstituted amino such that the moiety according to Formula VI is a urea or thiourea; or $R_{17}$ is alkoxy, aralkyloxy, aryloxy, substituted aralkyloxy, or substituted aryloxy, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide; and $R_{18}$ is alkyl, cycloalkyl, aralkyl, or aryl, with or without substituents or heteroatoms.

The furanosyl moieties independently can be in the D-configuration or in the L-configuration, with the D-configuration preferred. When $D_1$ and/or $D_2$ are oxygen, the furanose is preferably in the β-configuration and most preferably the furanose is in the β-D-configuration.

Preferred compounds of general Formula I are molecules whose structures fall within the definitions of Formula Ia:

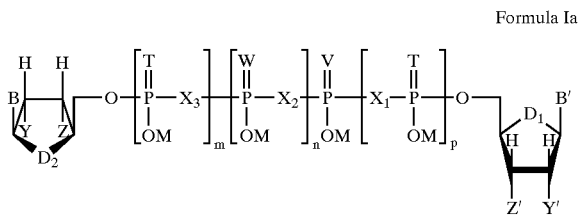

Formula Ia wherein:

M=H, or pharmaceutically-acceptable salt of this acid;

Z is H, or $OR_1$;

Z' is H, or $OR_3$;

Y is H, or $OR_2$;

Y' is H, or $OR_4$;

provided that at least one of Y, Y', Z, or Z' equals $OQ(R_5R_6R_7)$ under the definition of Formula II; or Y and Z taken together, and/or Y' and Z' taken together form a ring as defined in Formula III;

$D_1$=O;

$D_2$=O or C;

at least one of B or B' is an adenine residue according to Formula IV; and the sum of m+n+p is 3.

The most preferred compounds falling within Formula Ia, because of ease of synthesis and isolation, are those in which $T=V=W=X_1=X_2=X_3=$oxygen.

Preferred ether compounds of Formula Ia are those wherein $D_1=D_2=O$, B==B'=adenine, and $R_1$, $R_2$, $R_3$, and $R_4$ are independently H or $CR_5R_6R_7$, wherein $R_5=R_6=$H, and $R_7=$alkyl, aryl or arylalkyl, provided at least one of Y, Y', Z, and Z' is equal to $OCR_5R_6R_7$. For ether examples, most preferred compounds are selected from the group consisting of di-5'-[(2'-O-benzyl)adenosine] tetraphosphate, di-5'-[(3'-O-benzyl)adenosine] tetraphosphate, di-5'-[(2',3'-di-O-benzyl)adenosine] tetraphosphate, di-5'-[(2'-O-phenylethyl)adenosine] tetraphosphate, di-5'-[(3'-O-phenylethyl)adenosine] tetraphosphate, and di-5'-[(2',3'-di-O-phenylethyl)adenosine] tetraphosphate. Preferred ether compounds can also be selected from the group consisting of: $P^1$-5'-(2'-O-benzyl)adenosine-$P^4$-5"-adenosine tetraphosphate, $P^1$-5'-(3'-O-benzyl)adenosine-$P^4$-5"-adenosine tetraphosphate, $P^1$-5'-(2'-O-benzyl)adenosine-$P^4$-5"-(3"-O-benzyl)adenosine tetraphosphate, $P^1$-5'-(2'-O-phenylethyl)adenosine-$P^4$-5"-adenosine tetraphosphate, $P^1$-5'-(3'-O-phenylethyl)adenosine-$P^4$-5"-adenosine tetraphosphate, and $P^1$-5'-(2'-O-phenylethyl)adenosine-$P^4$-5"-(3"-O-phenylethyl)adenosine tetraphosphate.

Preferred ester compounds of Formula Ia are those wherein $D_1=D_2=O$, B==B'=adenine, and $R_1$, $R_2$, $R_3$, and $R_4$ are independently H or $CR_5R_6R_7$, wherein $R_5$ and $R_6$ are taken together as oxygen, and $R_7=$alkyl, aryl or arylalkyl, provided at least one of Y, Y', Z, and Z' is equal to $OCR_5R_6R_7$. For example, preferred ester compounds are selected from the group consisting of: di-5'-[(2'-O-benzoyl)adenosine] tetraphosphate, di-5'-[(3'-O-benzoyl)adenosine] tetraphosphate, di-5'-[(2',3'-di-O-benzoyl)adenosine] tetraphosphate, di-5'-[(2'-O-phenylacetyl)adenosine] tetraphosphate, di-5'-[(3'-O-phenylacetyl)adenosine] tetraphosphate, and di-5'-[(2',3'-di-O-phenylacetyl)adenosine] tetraphosphate. Other preferred ester compounds are selected from the group consisting of $P^1$-5'-(2'-O-benzoyl)adenosine-$P^4$-5"-adenosine tetraphosphate, $P^1$-5'-(3'-O-benzoyl)adenosine-$P^4$-5"-adenosine tetraphosphate, $P^1$-5'-(2'-O-benzoyl)adenosine-$P^4$-5"-(3"-O-benzoyl) adenosine tetraphosphate, $P^1$-5'-(2'-O-phenylacetyl) adenosine-$P^4$-5"-adenosine tetraphosphate, $P^1$-5'-(3'-O-phenylacetyl)adenosine-$P^4$-5"-adenosine tetraphosphate, and $P^1$-5'-(2'-O-phenylacetyl)adenosine-$P^4$-5"-(3"-O-phenylacetyl)adenosine tetraphosphate.

Other preferred compounds of Formula I are molecules whose structures fall within the definitions of Formula Ib:

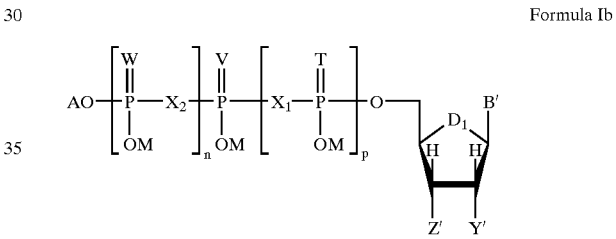

Formula Ib wherein:

A=M;

$X_1$ and $X_2$=O;

T, V, and W=O;

M=H or a pharmaceutically-acceptable salt of this acid;

Y' is H, or $OR_4$;

Z' is H, or $OR_3$;

with the provision that at least one of $R_3$ or $R_4$ is a residue according to Formula II;

or that $R_3$ and $R_4$ taken together form a ring as defined in Formula III;

$D_1$=O or C;

B' is an adenine residue according to Formula IV; and the sum of n+p is 2.

The most preferred compounds falling within Formula Ib, because of ease of synthesis and isolation, are those in which $T=V=W=X_1=X_2=X_3=$oxygen.

Preferred ether compounds of Formula Ib are those wherein $D_1=O$, B'=adenine, and $R_3=R_4=$H, alkyl, aryl or arylalkyl, provided that one of $R_3$ and $R_4$ is not H, further provided at least one of Y' and Z' equals to $OR_3$ or $OR_4$. For example, preferred compounds are selected from the group consisting of 5'-(2'-O-benzyl)adenosine triphosphate, 5'-(3'-O-benzyl)adenosine triphosphate, 5'-(2',3'-di-O-benzyl)adenosine triphosphate, 5'-(2'-O-phenylethyl)adenosine triphosphate, 5'-(3'-O-phenylethyl)adenosine triphosphate, and 5'-(2',3'-di-O-phenylethyl)adenosine triphosphate.

Preferred ester compounds of Formula Ib are those wherein $D_1=O$, B==B'=adenine, and $R_3$ and $R_4$ are independently H or $CR_5R_6R_7$, provided at least one of Y' and Z' equals to $OCR_5R_6R_7$, wherein $R_5$ and $R_6$ are taken together as oxygen, and $R_7=$alkyl, aryl or arylalkyl. For example, preferred compounds are selected from the group consisting of: 5'-(2'-O-benzoyl)adenosine triphosphate, 5'-(3'-O-benzoyl)adenosine triphosphate, 5'-(2',3'-di-O-benzoyl)adenosine triphosphate, 5'-(2'-O-phenylacetyl)adenosine triphosphate, 5'-(3'-O-phenylacetyl)adenosine triphosphate, and 5'-(2',3'-di-O-phenylacetyl)adenosine triphosphate.

Other preferred compounds of Formula I are molecules whose structures fall within the definitions of Formula Ic:

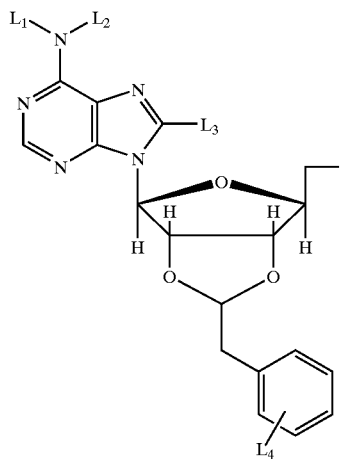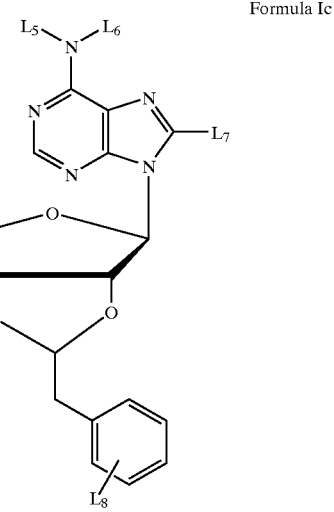

Formula Ic wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ and $L_8$ are independently selected from the group consisting of H, $C_1$–$C_6$ alkyl, aryl, $C_1$–$C_3$ alkylthio, $CF_3$, $CF_2CF_3$, —CN and —$N_3$.

A preferred compound of Formula Ic is that wherein $L_1=L_2=L_3=L_4=L_5=L_6=L_7=L_8=H$.

Other preferred compounds of Formula I are molecules whose structures fall within the definitions of Formula Id, or a 2'-ester or ether thereof, or 3'-ester or ether thereof:

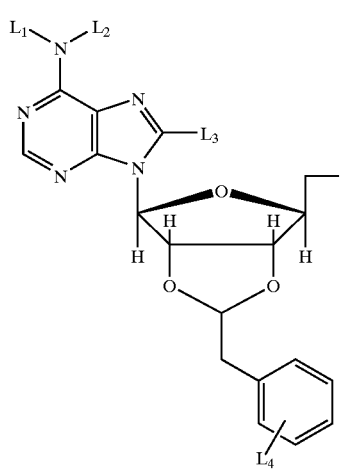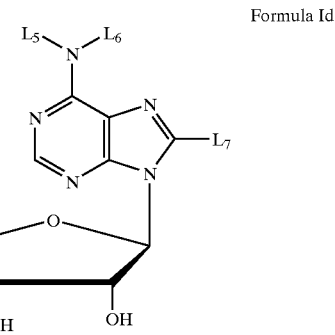

Formula Id wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

A particularly-preferred compound of Formula Id is one wherein $L_1$=$L_2$=$L_3$=$L_4$=$L_5$=$L_6$=$L_7$=H.

Further preferred compounds of Formula I are molecules whose structures fall within the definitions of Formula Ie:

Formula Ie

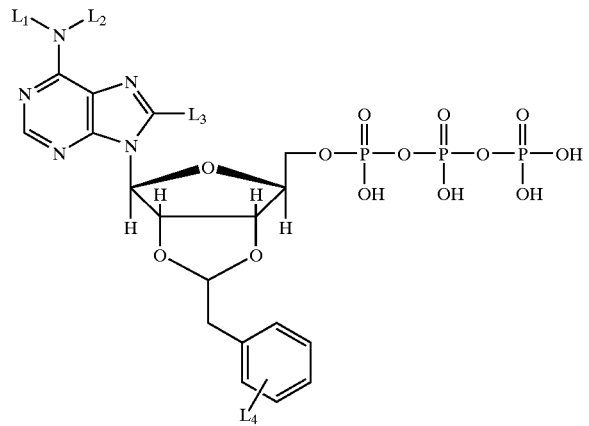

wherein $L_1$ and $L_2$ are independently selected from the group consisting of H, $C_1$–$C_4$ alkyl, phenyl, $C_1$–$C_{12}$ acyl and benzoyl;

$L_3$ is selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

A preferred compound of Formula Ie is that wherein $L_1$=$L_2$=$L_3$=$L_4$=H.

In general, alkyl groups include 1 to 8 carbons, either straight chained or branched, with or without unsaturation and with or without heteroatoms;

cycloalkyl groups include from 3 to 8 carbons, with or without unsaturation, and with or without heteroatoms, aralkyl groups include from 1 to 5 carbons in the alkyl portion, and with monocyclic or polycyclic moieties from 4 to 8 carbons per ring, with or without heteroatoms in the aryl portion;

aryl groups include cyclic moieties from 4 to 10 carbons, with or without heteroatoms; and these groups may or may not bear substituents;

Unless otherwise constrained by a limitation of the alkyl group, alkyl can optionally be substituted with from 1 to 3 substituents selected from the group consisting of hydroxy, ($C_{1-3}$) alkoxy, trifluoromethyl, ($C_{1-3}$)thioalkyl, halo, acyl, acyloxy, amino, aminoacyl, acylamino, alkoxycarbonyl, carboxyl, cyano, phenyl optionally substituted with 1 to 2 halo atoms and trifluoromethyl.

Unless otherwise constrained by the definition for the individual substituent, aryl, cycloalkyl, heteroaryl, and heterocyclic groups can be optionally substituted with 1 to 3 substituents selected from the group consisting of alkyl, alkenyl, aryl, cycloalkyl, cycloalkenyl, heteroaryl, heterocyclic, aralkyl, alkoxy, aryloxy, halo, nitro, hydroxy, amino, acyl, acyloxy, aminoacyl, acylamino, carboxy, cyano, alkoxycarbonyl, thioalkyl, thiophenyl and the like.

Preferred substituents include alkyl, alkoxy, halo, cyano, nitro, hydroxy, trihalomethyl, thioalkyl, and amino.

Substituents on the foregoing groups can be, but are not limited to, hydroxy, nitro, methoxy, fluoro, chloro, bromo, iodo, methyl, ethyl, propyl, butyl, benzyl, thioalkyl, alkoxy, carboxyl, cyano, amino, substituted amino, trifluoromethyl, phenyl, cyclopropyl, cyclopentyl, and cyclohexyl.

Preferred heteroatoms are oxygen, nitrogen, and sulfur, with oxygen being most preferred.

The present invention also encompasses non-toxic pharmaceutically acceptable salts of the above nucleotide and dinucleotide derivatives such as, but not limited to, alkali metal salts such as lithium, sodium or potassium salts, or alkaline earth metal salts such as magnesium or calcium salts; or ammonium or mono-, di-, tri- or tetraalkyl ammonium salts, such as $NH_4^+$, $NEH_3^+$, $NE_2H_2^+$, $NE_3H^+$, or $NE_4^+$ (wherein E is $C_{1-4}$ alkyl) salts. Pharmaceutically acceptable salts are salts that retain the desired biological activity of the parent compound and do not impart undesired toxicological effects. Preferred counterions are monovalent ions such as sodium, lithium or potassium.

The present invention also further encompasses non-toxic pharmaceutically acceptable esters and amides of the above nucleotide and dinucleotide derivatives such as, but not limited to, acetate esters or acetamides; formate esters or formamides, benzoate esters or benzamides, or pentanoate esters or pentanamides.

Methods of Preparing the Compounds

The compounds of the present invention can be conveniently synthesized by those skilled in the art using well-known chemical procedures. Mononucleoside mono-, di- and triphosphates, phosphonic acid derivatives and imidotriphosphates can be obtained from commercial sources or synthesized from the nucleoside using a variety of phosphorylation reactions found in the chemical literature. Symmetrical and unsymmetrical dinucleotide polyphosphates can be prepared by activation of a nucleoside mono-, di- or triphosphate with a coupling agent such as, but not limited to, dicyclohexylcarbodiimide or 1, 1'-carbonyldiimidazole, followed by condensation with another nucleoside mono-, di-, or triphosphate, which can be the same as or different from the activated moiety. Activation of nucleoside triphosphates with dicyclohexylcarbodiimide gives a cyclical trimetaphosphate as the activated species, which can react with a variety of nucleophiles to install unique substituents on the terminal phosphate of a triphosphate.

The compounds of the present invention can be prepared by derivatization or substitution at the level of the nucleoside, followed by phosphorylation and condensation as previously described; the reactions can alternatively be carried out directly on the preformed mono- or dinucleotides.

In Formulas Ia and Ib, the substituents at Y', Z', Y, and Z generally are, but are not limited to, alcohols, ethers, esters, carbamates, carbonates, or acetals where the substituents on oxygen are generally described by Formula II and/or Formula III. The substituents can be introduced as follows:

Ethers can be readily prepared by reacting a hydroxyl group of the furanose in a nucleoside with an alkylating agent in the presence of a suitable base in an appropriate solvent.

Esters can be readily prepared by reacting a hydroxyl group of the furanose in a nucleoside or nucleotide with an activated form of an appropriate organic acid, such as an acid halide or acid anhydride in the presence of an organic or inorganic base. Alternately, a suitable coupling reagent such as dicyclohexylcarbodiimide, or 1,1'- carbonyldiimidazole can be used to activate the organic acid to achieve similar results.

Carbamates or thiocarbamates can be most conveniently prepared by reaction of a hydroxyl group of the furanose in a nucleoside or nucleotide with any of a number of commercially available isocyanates or isothiocyanates, respectively, in an inert solvent. Alternately, when a desired isocyanate or isothiocyanate is not obtainable from commercial sources, it can be prepared from the corresponding amine by the use of phosgene or thiophosgene, or a chemical equivalent, respectively.

Carbonates or thiocarbonates can be synthesized by reacting the hydroxyl group of a furanose in a nucleoside or nucleotide with an appropriate haloformate in the presence of an organic or inorganic base.

Nucleosides can be converted into nucleotide monophosphates using phosphorous oxychloride in trimethyl phosphate. Hydrolysis and workup, followed by chromatographic purification gives the corresponding monophophate derivatives. Monophosphates can be further modified to give di- or triphosphates, phosphonic anhydride derivatives, phosphonamide derivatives, dinucleotide polyphosphates, dinucleotide phosphonate/phosphate anhydrides, or dinucleotide imidophosphate derivatives using literature procedures.

In Formulas I, Ia and Ib, the substituents at Y' and Z', and/or Y and Z, are optionally taken together to form acetals, ketals or orthoesters. Acetals and ketals can be readily prepared by reaction of adjacent 2'- and 3'-hydroxyl groups of the furanose in an appropriate nucleoside or nucleotide with an aldehyde or ketone, or their chemical equivalents, respectively, in the presence of an acid catalyst. Particularly advantageous is to use an organic acid such as formic acid, which can effect the transformation without completely affecting the integrity of the rest of the molecule. Alternately, strong acids such as trichloroacetic, p-toluenesulfonic, methanesulfonic and the like can be employed in catalytic amounts, in conjunction with inert solvents. In some cases it is preferable to use a strong acid in combination with another acid such as formic acid.

Similarly, cyclical orthoesters can be prepared by reaction of adjacent 2'- and 3'-hydroxyl groups of a furanose with an acylic orthoester in the presence of an acid.

When the nucleoside or nucleotide to be derivatized is a purine that contains a 6-amino functionality or is a pyrimidine that contains a 4-amino functionality, it can be converted to the respective urea or thiourea by treatment with isocyanates or isothiocyanates, respectively, as was previously described for carbamates or thiocarbamates of the 2'- or 3'-hydroxyls and/or 2" or 3" hydroxyls of the furanose rings. It has been found that reactions of the amino group with isocyanates or isothiocyanates can be carried out in the presence of the hydroxyl groups of the furanose, by appropriate manipulation of the stoichiometry of the reaction.

All of the derivatization reactions described can be carried out on preformed dinucleotide polyphosphates, which result in multiple products. Relative product ratios depend upon reaction stoichiometry and on whether multiple reactive groups are present. When multiple products are obtained, these can be conveniently separated by the use of preparative reverse-phase high performance liquid chromatography (HPLC). Particularly advantageous is the use of C18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Furthermore, the use of ammonium acetate buffer solutions in conjunction with methanol allows the chromatographed products to be isolated following evaporation and lyophilization of the volatile salt.

While separation of multiple products can be done by HPLC, another strategy to increase the yield of desired product from a reaction sequence is to first introduce protecting groups into nucleoside- or nucleotide-starting materials. This strategy can produce materials, which have a single reactive functionality available for reaction with a subsequent reagent. Protecting groups can be introduced on preformed dinucleotide polyphosphates, or alternately, can be carried out on nucleoside mono-, di-, or triphosphates. These materials can be purified by chromatography or other means. Further functionalization, followed by deprotection leads to a selectively-functionalized product. This new material can be used in further condensation reactions, or can be the end product desired in the sequence.

Those having skill in the art will recognize that the starting materials can be varied and additional steps employed to produce compounds encompassed by the present invention. In some cases protection of certain reactive functionalities may be necessary to achieve some of the above transformations. In general the need for such protecting groups will be apparent to those skilled in the art of organic synthesis as well as the conditions necessary to attach and remove such groups.

Methods of Administration

The active compounds disclosed herein are administered to a painful area of a patient by any suitable means, but are preferably introduced by administering a liquid or gel suspension of the active compound in the form of injection, drops, spray, foam or gel. Alternatively, liposomes containing the active compounds may be applied to the painful area to reduce pain. Further, the active compounds may be infused into the painful area via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses that are placed on the eye, or adhesive bandages, gauzes or sponges placed on skin or an exposed layer of cells. Another embodiment of the present invention involves an active compound of this invention placed on or within a swab or sponge that can be used to apply the pain-reducing material to the painful area. Another embodiment of the present invention comprises the active compound contained within a liquid spray or foam, which can be applied to the painful area. Another embodiment of the present invention involves an injection of the active compound directly into the painful area, or onto or under the surface of the painful area.

In another embodiment of the present invention the active compound is formulated for vaginal administration. Pessaries, tampons, sponges, creams, gels, pastes, foams or sprays containing in addition to the active compound such carriers as are known in the art to be appropriate are included in this embodiment of the invention.

In a further embodiment of the present invention the active compound is formulated for administration as a suppository. A low melting wax, such as a mixture of fatty acid glycerides or cocoa butter is first melted and the active compound is homogeneously dispersed. The molten homogeneous mixture is then poured into conveniently sized molds, and then allowed to cool and solidify.

The quantity of the active compound included in the pharmaceutical composition of the present invention is an amount that is effective in reducing pain. Actual dosage levels of active compounds in the pharmaceutical compositions of this invention can be varied so as to obtain an amount of the active compound(s) that is effective to achieve the desired therapeutic response for a particular patient given that particular composition and mode of administration. The selected dosage level will depend upon the activity of the particular compound, the route of administration, the severity of the condition being treated and the condition and prior medical history of the patient being treated. However, it is generally known to those skilled in the art to start doses of the compound at levels lower than required to achieve the desired therapeutic effect and to gradually increase the drug dosage until the desired effect is achieved. The dosage amount is preferably an amount sufficient to achieve dissolved concentrations of the active compound in the painful area of the subject from about $10^{-10}$ to about $10^{-1}$ moles/liter, and more preferably from about $10^{-6}$ to about $10^{-1}$ moles/liter, in order to treat or significantly diminish the pain response in that area. If desired, the effective daily dose can be divided into multiple doses for purposes of administration; consequently, single dose compositions may contain such amounts or submultiples thereof to make up the daily dose.

A topical solution containing an active compound optimally contains a physiologically compatible vehicle, as those skilled in the dermal and ophthalmic art can select using conventional criteria. The vehicles are selected from the known ophthalmic and cutaneous vehicles which include, but are not limited to, saline solutions, water, polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil, polysaccharides such as dextrans, glycosaminoglycans such as sodium hyaluronate, and salts such as sodium chloride and potassium chloride.

In addition to the above listed methods of administration, the following various methods can be used for administering effective amounts of a compound of Formula I for pain relief via either topical or systemic routes of administration. One such means of administration is by inhalation of an aerosol suspension of respirable particles comprising a pharmaceutically effective amount of the active compound. The active compound can directly act on a painful area on the surface of the lungs or be absorbed into the bloodstream via the lungs, and subsequently diminish the pain in a painful area of the body. The respirable particles may be liquid or solid, with a particle size sufficiently small to pass through the mouth and larynx upon inhalation; in general, particles ranging from about 1 to 10 microns in diameter, but more preferably 1–5 microns in diameter are considered respirable. Alternatively, the active compound can directly act on a painful area on the surface of the throat, oropharynx, or upper airway by inhalation of larger particles comprising active compound(s). When the particle size of the composition is chosen in the range from about 10 to 200 microns in diameter, but more preferably 20 to 100 microns in diameter, the particles and active component are deposited onto the epithelial layers of the throat and upper airway, providing a method for relieving pain in those areas.

A further method may be by nasal administration. The solutions or suspensions of active compound(s) are applied directly to the nasal cavity by conventional means, for example, with a dropper, pipette or spray. The formulation may be provided in single or in multidose forms. In the case of dosing by a dropper or pipette, an appropriate, predetermined volume of the solution or suspension may be administered. Alternately, a spray may be delivered, for example, by means of a metered, atomizing spray pump or other known methods such as by inhalation of a mist comprising the active material, as generated by a spray bottle.

Means of administering the active compounds to the eyes of a subject comprises administering a liquid/liquid suspension or other pharmaceutically acceptable formulation in the form of eye drops or eyewash to the eye(s) of a subject in need of such treatment. Alternatively, nasal drops of a liquid formulation, or a nasal spray of respirable particles that the subject inhales can be used to treat painful areas of the nose, nasal passageways or sinuses. Liquid pharmaceutical compositions of the active compound for use in a nasal spray, nasal drops or eye drops may be prepared by combining the active compound with a suitable vehicle, such as sterile pyrogen-free water or sterile saline by techniques known to those skilled in the art.

Means of oral administration of active compound comprises pharmaceutical compositions containing an active compound or compounds in the form of tablets, lozenges, aqueous or oily suspensions, dispersible powders or granules, emulsions, hard or soft capsules, syrups or elixirs. Compositions intended for oral use can be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Administration of an active compound to relieve pain in a subject may also be in the form of a suppository comprising the active compound, such that a therapeutically effective amount of the compound diminishes the pain in an area of a subject in need of such pain relief.

Administration of the active compound via direct intraoperative instillation of a gel, cream, or liquid suspension of a therapeutically effective amount of the active compound is another embodiment of this invention. The active compound may be applied to an area requiring analgesia during pre-operative, operative and/or post-operative procedures via a suitable delivery method. The active compound, formulated with an acceptable carrier as is known in the art to be appropriate, would be delivered either by a single administration, or using a continuous or selective-release device. Such devices may be, but are not limited to, syringes, sprayers, adhesive bandages, sponges or swabs.

The method of the present invention can be used with other therapeutic and adjuvant agents commonly used to reduce pain, thus enhancing the effects of the therapeutic agents and adjunctive agents. Examples of other therapeutic agents used in the treatment of pain include opioids (Morphine, Fentanyl), sodium channel blockers (Novocaine, Lidocaine), NSAIDS (aspirin, ibuprofen) and COX2 inhibitors (Vioxx, Celebrex).

High doses are sometimes required for therapeutic agents to achieve the desired levels of analgesic response, but high drug doses are often associated with a greater frequency of dose-related adverse effects. Thus, combined use of the compounds of the present invention with other therapeutic agents commonly used to treat pain may allow the use of lower doses of other pain-relieving agents to achieve similar or reduced levels of pain in a subject in need of such treatment; this combination therapy may also reduce the frequency of adverse side effects associated with long-term administration of such agents. Thus, another advantage of the use of the compounds in this invention may be to reduce the number and/or severity of such side effects as tolerance, dependence, constipation, respiratory depression, sedation, and/or gastrointestinal side effects from drugs used to treat pain.

It is understood that the foregoing detailed description and accompanying examples are merely illustrative and are not to be taken as limitations upon the scope of the invention, which is defined solely by the appended claims and their equivalents.

Various changes and modifications, including without limitation those relating to the chemical structures, substituents, derivatives, intermediates, syntheses, formulations and/or methods of use of the invention, may be made without departing from the spirit and scope thereof.

EXAMPLES

Example 1

Effects of AP4AmA in the Hotplate Assay for Acute Pain in Mice

The action of $P^1$-5'-[2'-(O)—,3'-(O)-(benzyl) methylenedioxy]adenosine-$P^4$-5''-adenosine tetraphosphate, (AP4AmA; $AP_4A$-2', 3'-mono-acetal with phenylacetaldehyde) on mice in the hotplate model illustrates the analgesic affect of compounds of Formula I. The temperature of the hot plate was set at 55 degrees Celsius. Animals were administered subcutaneously AP4AmA or saline into the dorsal aspect of both hind paws in a volume of 20 microliters. This administration occurred 5 minutes prior to placement on the hotplate. Morphine was administered subcutaneously into the back nape of the mouse's neck in a volume of 10 mL/kg.

The time to hindpaw lick was used as the efficacy endpoint. If the animals did not lick their hindpaws after 36 seconds then they were considered to be fully protected to the hotplate induced algesia. The raw averages were then converted to a maximum percent effect, MPE %, by normalizing the response to vehicle as baseline and 36 seconds as fully protected.

FIG. 1 shows the antinociceptive effect of administration of $AP_4AmA$ ($AP_4A$-2', 3'-monoacetal with phenylacetaldehyde) and morphine in the mouse in a preclinical model of acute nociception (the hotplate model). The results clearly illustrate a dose dependent pharmacological effect of AP4AmA in increasing the time to hindpaw lick, maximal percent effect, in the hotplate. This effect is statistically equivalent to morphine at the highest dose of AP4AmA and statistically significant from vehicle control. This example demonstrates that compounds of Formula I are effective in treating or preventing acute pain.

Example 2

Effects of AP4AmA on the Abdominal Constriction Assay for Visceral Pain in Mice

These examples illustrate the effects of $AP_4AmA$ in two similar models of abdominal constriction; acetic acid-induced and phenylbenzoquinone-induced constrictions in mice. The method employed in FIGS. 2A and 23B was a modification of the abdominal constriction test described by Collier et. al (Collier, H, O. et. al, *Br. J. Pharmacol. Chemother.* 32:295–310 (1968)).

Figure 2A:
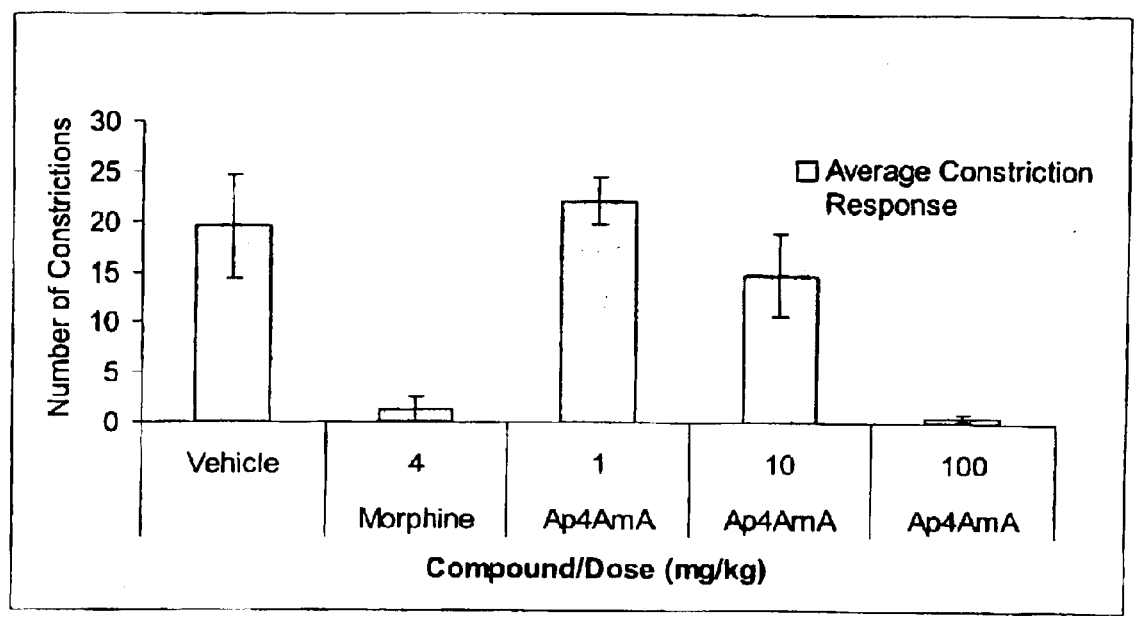
FIG. 2A shows the antinociceptive effect of administration of $AP_4AmA$ and morphine in the acetic acid induced constriction assay in mice.

Briefly, in FIG. 2A, each animal, received an intraperitoneal (i.p.) injection of 0.9% acetic acid in a volume of 10 mL/kg. The mouse was placed in an observation chamber shortly after the acetic acid injection and allowed to explore. Testing started five minutes after the acetic acid injection and consisted of 10 minutes of observation during which the number of abdominal constrictions was counted. Abdominal constriction was defined as a lengthwise stretching of the torso with concave arching of the back. AP4AmA and vehicle were administered i.p., in a volume of 10 mL/kg, 3 minutes prior to the administration of acetic acid while Morphine was administered i.p., in a volume of 10 mL/kg, 25 minutes prior to the administration of acetic acid.

Figure 2B:
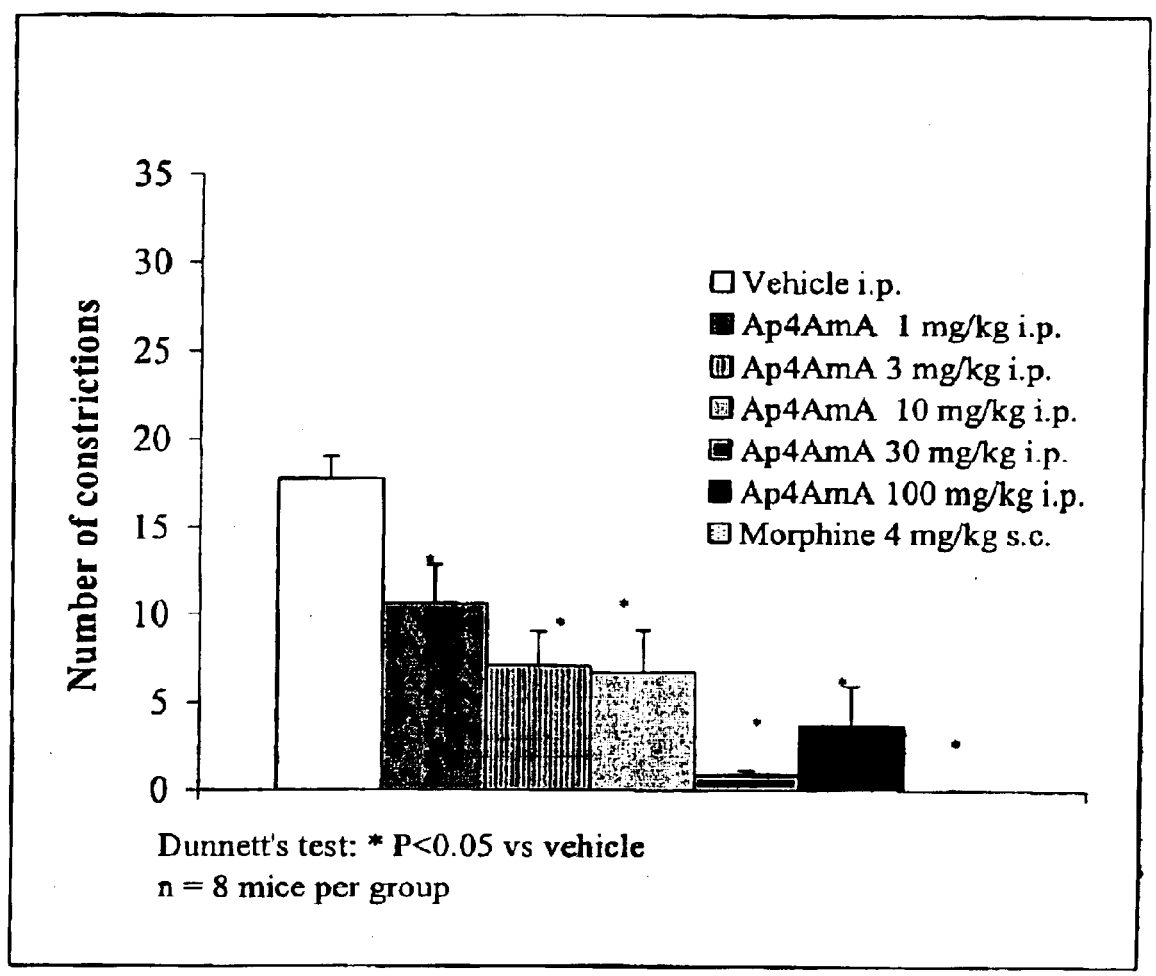
FIG. 2B shows the antinociceptive effect of administration of $AP_4AmA$ and morphine in the phenylbenzoylquinone induced constriction assay in mice.

Briefly, in FIG. 2B, each animal received an i.p. injection of 0.02% phenylbenzoquinone in a volume of 10 mL/kg. The mouse was placed in an observation chamber shortly after the acetic acid injection and allowed to explore. Testing started five minutes after the acetic acid injection and consisted of 5 minutes of observation during which the number of abdominal constrictions was counted. Abdominal constriction was defined as a lengthwise stretching of the torso with concave arching of the back. AP4AmA and vehicle were administered i.p., in a volume of 10 mL/kg, 3 minutes prior to the administration of acetic acid while morphine was administered i.p., in a volume of 10 mL/kg, 30 minutes prior to the administration of acetic acid.

The results above clearly illustrate a dose dependent pharmacological effect of AP4AmA in reducing the abdominal constrictions in both the acetic acid and phenylbenzoylquinone-induced constrictions. This effect is not statistically different from morphine at 100 mg/kg AP4AmA in the acetic acid model and 30 mg/kg AP4AmA is not statistically different from morphine in the phenylbenzoquinone model. This example demonstrates that compounds of Formula I are effective in treating or preventing visceral pain.

Example 3

Effects of AP4AmA on the Formalin Assay for Inflammatory Pain in Mice

This example illustrates the effect of AP4AmA in mice in phase II of the formalin assay for persistent inflammatory pain. In brief, mice were injected 20 microliters of a 5% full strength formalin solution subcutaneously (s.c.) into the dorsal aspect of the right hindpaw. The mice were returned to the observation cage. The mice were injected 10 microliters s.c. into the same dorsal aspect of the right hindpaw with either vehicle or AP4AmA in varying concentrations 10 minutes after the formalin injection. They were returned to the observation cages and the number of times they licked their right hind foot was counted from the 10 minutes to the 30 minutes post formalin administration.

Figure 3:
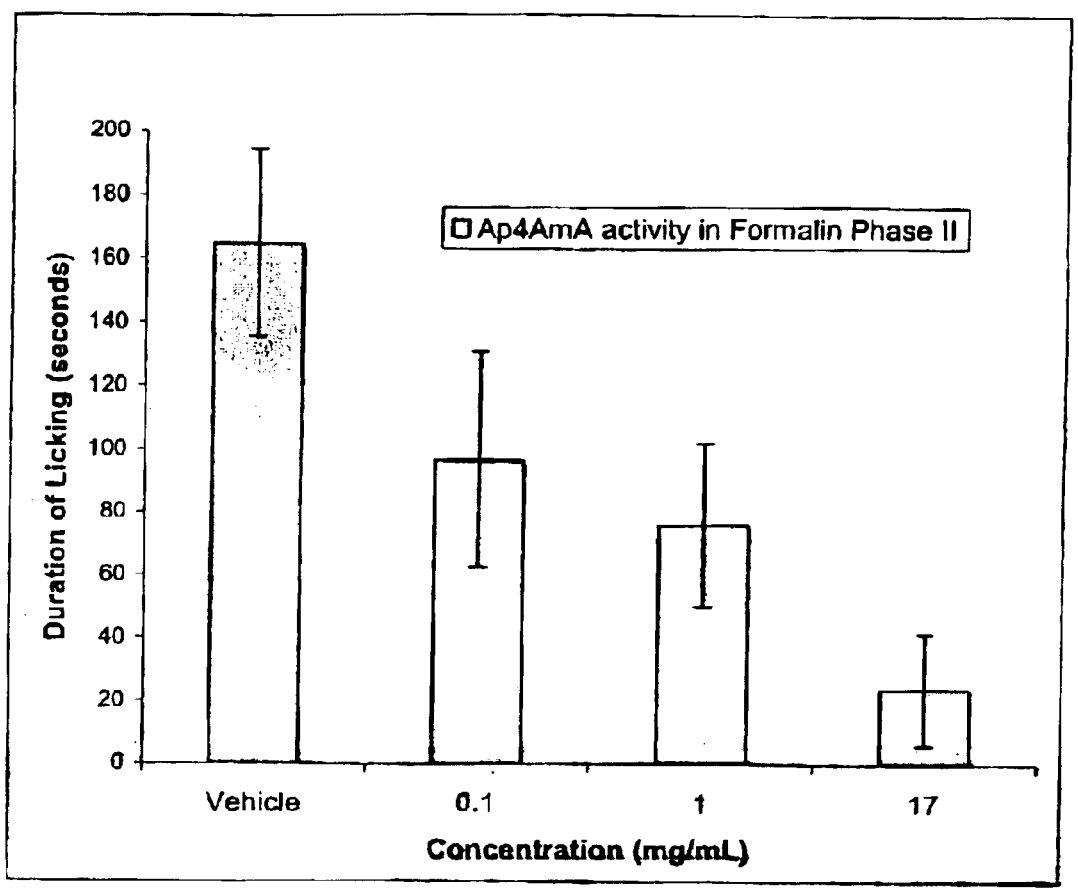
FIG. 3 shows the action of $AP_4AmA$ in the mouse in a preclinical model of inflammatory somatic pain (the formalin model, persistent pain phase).

FIG. 3 shows the action of AP4AmA in the mouse in a preclinical model of inflammatory somatic pain (the formalin model, persistent pain phase). The results clearly illustrate a dose dependent pharmacological effect of AP4AmA in reducing the duration of time spent licking the inflamed hind paw. This example demonstrates that compounds of Formula I are effective in treating or preventing inflammatory somatic pain.

Example 4

Effects of AP4AmA on the Spinal Nerve (L5/L6) Ligation Model for Neuropathic Pain in Rats This example illustrates the effect of AP4AmA in rats in a tactile allodynia model of nerve ligation model described in detail by Kim and Chung (Kim and Chung, *Pain* 50:355–363 (1992)). Mechanical (tactile) allodynia was measured by using electronic calibrated von Frey filaments.

AP4AmA was administered subplantar 60 minutes prior to allodynia testing where as morphine was administered i.p. 60 minutes prior to testing. FIG. 5 illustrates that AP4AmA administered in a concentration of 0.03 mg/mL in a volume of 50 microliters directly to the paw can reverse the allodynia in the rat to an equivalent level as morphine administered i.p. at 16 mg/kg.

Figure 4:
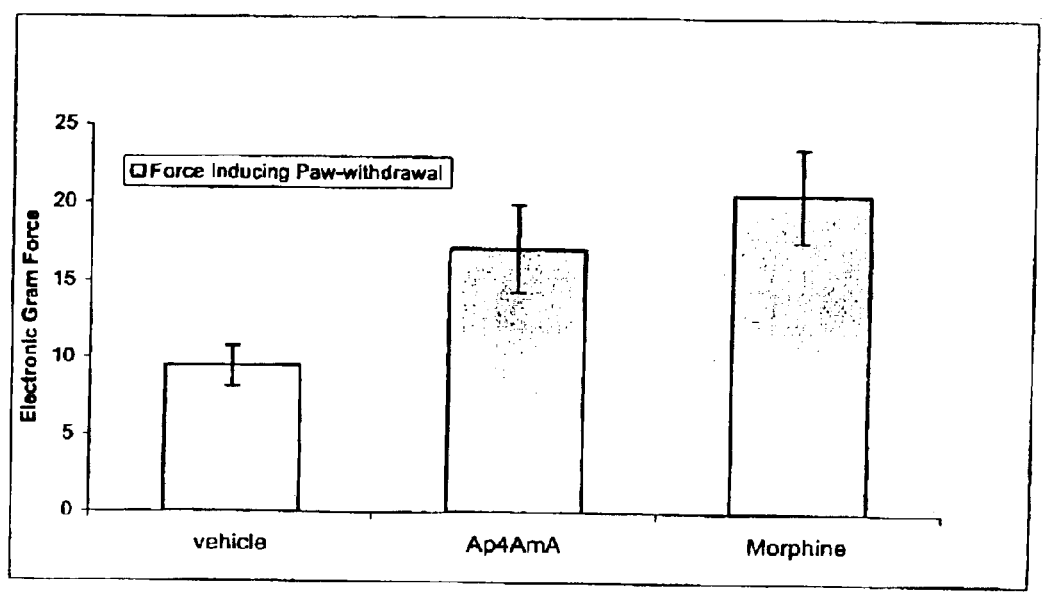
FIG. 4 shows the action of AP4AmA in the rat in a preclinical model of neuropathic pain (the Spinal Nerve (L5/L6) Ligation model).

FIG. 4 shows the action of $AP_4AmA$ in the rat in a preclinical model of neuropathic pain (the Spinal Nerve (L5/L6) Ligation model). The results clearly illustrate a pharmacological effect of AP4AmA in enhancing the gram force required to induce the rat to withdrawal the allodynic hindpaw. This effect is not statistically different from morphine and significantly different from vehicle control. This example demonstrates that compounds of Formula I are effective in treating neuropathic pain.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A method of treating pain comprising administering to a subject a pharmaceutical composition comprising an effective amount of a compound of Formula I, or a pharmaceutically acceptable salt, or amide or ester thereof:

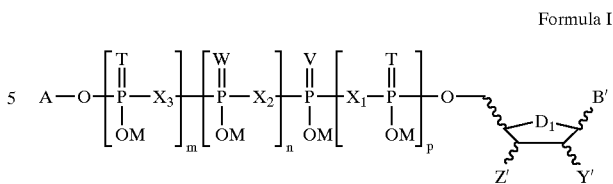

Formula I wherein:
$X_1$, $X_2$, and $X_3$ are independently oxygen, methylene, monochloromethylene, dichloromethylene, monofluoromethylene, difluoromethylene, or imido;
T, W, and V are independently oxygen or sulfur;
m=0, 1 or 2;
n=0 or 1;
p=0, 1, or 2;
where the sum of m+n+p is from 0 to 5;
each M is independently hydrogen or a pharmaceutically-acceptable inorganic or organic counterion;
A=M, or
A is a nucleoside residue which is defined as:

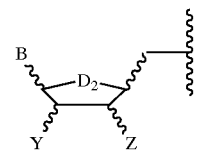

and is linked to the phosphate chain via the 5' position of the furanose or carbocycle;
Z is H, F or $OR_1$;
Z' is H, F or $OR_3$;
Y is H, F or $OR_2$;
Y' is H, F or $OR_4$;
$R_1$, $R_2$, $R_3$, and $R_4$ are independently H or a residue according to Formulas II and/or III;
provided that when A=M, at least one of Y' and Z' equals $OQ(R_5R_6R_7)$ under the definition of Formula II; or Y' and Z' taken together form a ring as defined in Formula III;
further provided that when A is a nucleoside, at least one of Y, Y', Z, or Z' equals $OQ(R_5R_6R_7)$ under the definition of Formula II; or either Y and Z taken together, or Y' and Z' taken together form a ring as defined in Formula III;
$D_1$ and $D_2$ are independently O or C;

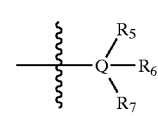

Formula II wherein:
Q is a carbon atom;
$R_5$, $R_6$, and $R_7$ are independently H, F, alkyl, cycloalkyl, aralkyl, aryl, substituted aralkyl, or heterocyclic moiety, or
$R_5$ and $R_6$, are taken together to form a carbocyclic or heterocyclic ring of 4 to 7 members, such that the moiety defined according to Formula II when attached to the oxygen is an ether; or $R_5$ and $R_6$ are taken together as oxygen or sulfur doubly bonded to Q, and $R_7$ is alkyl, cycloalkyl, aralkyl, substituted aralkyl, aryl, or a heterocycle of 4 to 7 members, such that the moiety defined according to Formula II when attached to the oxygen is an ester or thioester; with the provision that when $R_5$ and $R_6$ are taken together as oxygen, and A=M, and $X_1$=oxygen, then $R_7$ is not benzoylbenzoyl; or $R_5$ and $R_6$ are taken together as oxygen or sulfur doubly bonded to Q, and $R_7$ is amino or mono- or disubstituted amino, where the substituents are alkyl, cycloalkyl, aralkyl, aryl, substituted aralkyl, or substituted aryl, or where the substituents on nitrogen form a heterocyclic ring of 4 to 7 members such that the moiety according to Formula II when attached to the oxygen is a carbamate or thiocarbamate; or $R_5$ and $R_6$ are taken together as oxygen or sulfur doubly bonded to Q, and $R_7$ is alkoxy, cycloalkoxy, aralkyloxy, aryloxy, substituted aralkyloxy, or substituted aryloxy, such that the moiety according to Formula II when attached to the oxygen is a carbonate or thiocarbonate;

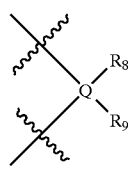

Formula III wherein $R_1$ and $R_2$ and/or $R_3$ and $R_4$ are taken together to form Q;

Q is a carbon atom;

$R_8$ and $R_9$ are taken together as oxygen or sulfur doubly bonded to Q to form a cyclical carbonate or thiocarbonate; or $R_8$ and $R_9$ can be taken together to form a ring of 4 to 7 members, with or without substituents, with or without unsaturation and with or without heteroatoms in the ring, with the provision that when A=M, and $X_1$=oxygen, said ring can have no more than two nitro groups as substituents or $R_8$ is hydrogen, alkyl, cycloalkyl, aryl, aralkyl, substituted aralkyl, or heterocycle;

$R_9$ is hydrogen, alkyl, cycloalkyl, aryl, aralkyl, substituted aralkyl, heterocycle, alkyloxy, cycloalkyloxy, aralkyloxy, aryloxy, substituted aralkyloxy, or substituted aryloxy, such that Q is part of an acetal-, ketal- or ortho ester moiety;

B and B' are independently a purine or a pyrimidine residue according to Formulas IV or V which is linked to the sugar via the 9- or 1-position, respectively;

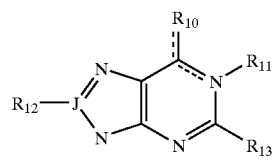

Formula IV

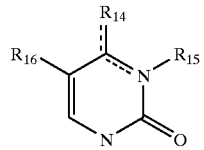

Formula V wherein:

$R_{10}$ and $R_{14}$ are independently hydroxy, oxo, amino, mercapto, alkylthio, alkyloxy, aryloxy, alkylamino, cycloalkylamino, aralkylamino, arylamino, diaralkylamino, diarylamino, N-alkyl-N-arylamino, or dialkylamino, where the alkyl and/or aryl groups are optionally linked to form a heterocycle; or $R_{10}$ and $R_{14}$ are independently acylamino, according to Formula VI; or when $R_{10}$ or $R_{14}$ has as its first atom nitrogen, $R_{10}$ and $R_{11}$ or $R_{14}$ and $R_{15}$ are taken together to form a 5-membered fused imidazole ring, optionally substituted on the imidazole ring of the etheno-compound with a substituted- or unsubstituted-alkyl, cycloalkyl, aralkyl, or aryl moiety, as described for $R_5$–$R_9$ above;

J is carbon or nitrogen, with the provision that when J is nitrogen, $R_{12}$ is not present;

$R_{11}$ is hydrogen, O or is absent;

when present, $R_{12}$ is hydrogen, alkyl, azido, amino, alkylamino, arylamino or aralkylamino, hydroxy, alkoxy, aryloxy or aralkyloxy, sulfhydryl, alkylthio, arythio or aralkylthio, or $\omega$-X($C_{1-6}$alkyl)G-, wherein X is subdtituted- or unsubstituted- amino, mercapto, hydroxy or carboxyl and G is chosen from —O—, —S—, —$NR_{18}$—, —$N(CO)R_{18}$—, or $N(CO)OR_{18}$—;

$R_{13}$ is hydrogen, chlorine, fluorine, hydroxy, amino, monosubstituted amino, disubstituted amino, alkylthio, trifluoroalkylthio, arylthio, or aralkylthio, where the substituent on sulfur contains up to a maximum of 20 carbon atoms, with or without unsaturation;

$R_{15}$ is hydrogen, or acyl;

$R_{16}$ is hydrogen, alkyl, halo, aryl, aralkyl, alkenyl, substituted alkenyl, alkynyl, or substituted alkynyl;

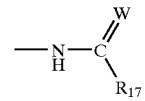

Formula VI wherein:

W is oxygen or sulfur;

$R_{17}$ is amino or mono- or disubstituted amino such that the moiety according to Formula VI is a urea or thiourea; or $R_{17}$ is alkoxy, aralkyloxy, aryloxy, substituted aralkyloxy, or substituted aryloxy, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide; and $R_{18}$ is alkyl, cycloalkyl, aralkyl, aryl, with or without substituents or heteroatoms.

2. The method according to claim 1, wherein at least one of B or B' is adenine.

3. The method according to claim 1, wherein said compound is a compound of Formula Ia:

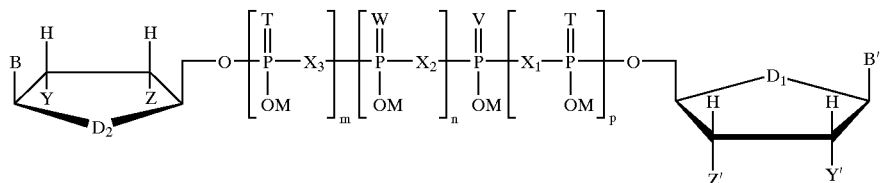

Formula Ia wherein:

M=H, or pharmaceutically-acceptable salt of this acid;

Z is H, or $OR_1$;

Z' is H, or $OR_3$;

Y is H, or $OR_2$;

Y' is H, or $OR_4$;

provided that at least one of Y, Y', Z, or Z' equals $OQ(R_5R_6R_7)$ under the definition of Formula II; or Y and Z taken together, and/or Y' and Z' taken together form a ring as defined in Formula III;

$D_1$=O;

$D_2$=O or C;

at least one of B or B' is an adenine residue according to Formula IV; and the sum of m+n+p is 3.

4. The method according to claim 3, wherein T=V=W=$X_1$=$X_2$=$X_3$=$D_1$=$D_2$ oxygen, B=B'=adenine, and $R_1$, $R_2$, $R_3$, and $R_4$ are independently H or $CR_5R_6R_7$, wherein $R_5$=$R_6$=H, and $R_7$=alkyl, aryl or arylalkyl, provided at least one of Y, Y', Z, and Z' is equal to $OCR_5R_6R_7$.

5. The method according to claim 4, wherein said compound is selected from the group consisting of di-5'-[(2'-O-benzyl)adenosine] tetraphosphate, di-5'-[(3'-O-benzyl)adenosine] tetraphosphate, di-5'-[(2',3'-di-O-benzyl)adenosine] tetraphosphate, di-5'-[(2'-O-phenylethyl)adenosine] tetraphosphate, di-5'-[(3'-O-phenylethyl)adenosine] tetraphosphate, and di-5'-[(2',3'-di-O-phenylethyl)adenosine] tetraphosphate.

6. The method according to claim 4, wherein said compound is selected from the group consisting of: $P^1$-5'-(2'-O-benzyl)adenosine-$P^4$-5"-adenosine tetraphosphate, $P^1$-5'-(3'-O-benzyl)adenosine-$P^4$-5"-adenosine tetraphosphate, $P^1$-5'-(2'-O-benzyl)adenosine-$P^4$-5"-(3"-O-benzyl)adenosine tetraphosphate, $P^1$-5'-(2'-O-phenylethyl)adenosine-$P^4$-5"-adenosine tetraphosphate, $P^1$-5'-(3'-O-phenylethyl)adenosine-$P^4$-5"-adenosine tetraphosphate, and $P^1$-5'-(2'-O-phenylethyl)adenosine-$P^4$-5"-(3"-O-phenylethyl)adenosine tetraphosphate.

7. The method according to claim 3, wherein T=V=W=$X_1$=$X_2$=$X_3$=$D_1$=$D_2$=oxygen, B=B'=adenine, and $R_1$, $R_2$, $R_3$, and $R_4$ are independently H or $CR_5R_6R_7$, wherein $R_5$ and $R_6$ are taken together as oxygen, and $R_7$=alkyl, aryl or arylalkyl, provided at least one of Y, Y', Z, and Z' is equal to $OCR_5R_6R_7$.

8. The method according to claim 7, wherein said compound selected from the group consisting of: di-5'-[(2'-O-benzoyl)adenosine] tetraphosphate, di-5'-[(3'-O-benzoyl)adenosine] tetraphosphate, di-5'-[(2',3'-di-O-benzoyl)adenosine] tetraphosphate, di-5'-[(2'-O-phenylacetyl)adenosine] tetraphosphate, di-5'-[(3'-O-phenylacetyl)adenosine] tetraphosphate, and di-5'-[(2',3'-di-O-phenylacetyl)adenosine] tetraphosphate.

9. The method according to claim 7, wherein said compound is selected from the group consisting of: $P^1$-5'-(2'-O-benzoyl)adenosine-$P^4$-5"-adenosine tetraphosphate, $P^1$-5'-(3'-O-benzoyl)adenosine-$P^4$-5"-adenosine tetraphosphate, $P^1$-5'-(2'-O-benzoyl)adenosine-$P^4$-5"-(3"-O-benzoyl) adenosine tetraphosphate, $P^1$-5'-(2'-O-phenylacetyl)adenosine-$P^4$-5"-adenosine tetraphosphate, $P^1$-5'-(3'-O-phenylacetyl)adenosine-$P^4$-5"-adenosine tetraphosphate, and $P^1$-5'-(2'-O-phenylacetyl)adenosine-$P^4$-5"-(3"-O-phenylacetyl)adenosine tetraphosphate.

10. The method according to claim 1, wherein said compound is a compound of Formula Ib:

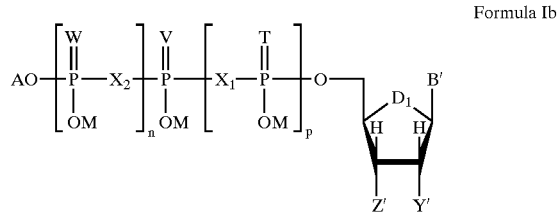

Formula Ib wherein:

A=M;

$X_1$ and $X_2$=O;

T, V, and W=O;

M=H or a pharmaceutically-acceptable salt of this acid;

Y' is H, or $OR_4$;

Z' is H, or $OR_3$;

with the provision that at least one of $R_3$ or $R_4$ is a residue according to Formula II;

or that $R_3$ and $R_4$ taken together form a ring as defined in Formula III;

$D_1$=O or C;

B' is an adenine residue according to Formula IV; and the sum of n+p is 2.

11. The method according to claim 10, wherein T=V=W=$X_1$=$X_2$=$X_3$=D=oxygen, B'=adenine, and $R_3$=$R_4$=H=alkyl, aryl or arylalkyl, provided at least one of Y' and Z' equals to $OR_3$ or $OR_4$, further provided that one of $R_3$ and $R_4$ is not H.

12. The method according to claim 11, wherein said compound selected from the group consisting of 5'-(2'-O-benzyl)adenosine triphosphate, 5'-(3'-O-benzyl)adenosine triphosphate, 5'-(2',3'-di-O-benzyl)adenosine triphosphate, 5'-(2'-O-phenylethyl)adenosine triphosphate, 5'-(3'-O-phenylethyl)adenosine triphosphate, and 5'-(2',3'-di-O-phenylethyl)adenosine triphosphate.

13. The method according to claim 10, wherein T=V=W=$X_1$=$X_2$=$X_3$=$D_1$=oxygen, B=B'=adenine, and $R_3$ and $R_4$ are independently H or $CR_5R_6R_7$, provided at least one of Y' and Z' equals to $OCR_5R_6R_7$, wherein $R_5$ and $R_6$ are taken together as oxygen, and $R_7$=alkyl, aryl or arylalkyl.

14. The method according to claim 13, wherein said compound is selected from the group consisting of: 5'-(2'-

O-benzoyl)adenosine triphosphate, 5'-(3'-O-benzoyl) adenosine triphosphate, 5'-(2',3'-di-O-benzoyl)adenosine triphosphate, 5'-(2'-O-phenylacetyl)adenosine triphosphate, 5'-(3'-O-phenylacetyl)adenosine triphosphate, and 5'-(2',3'-di-O-phenylacetyl)adenosine triphosphate.

15. The method according to claim 1, wherein said compound is a compound of Formula Ic:

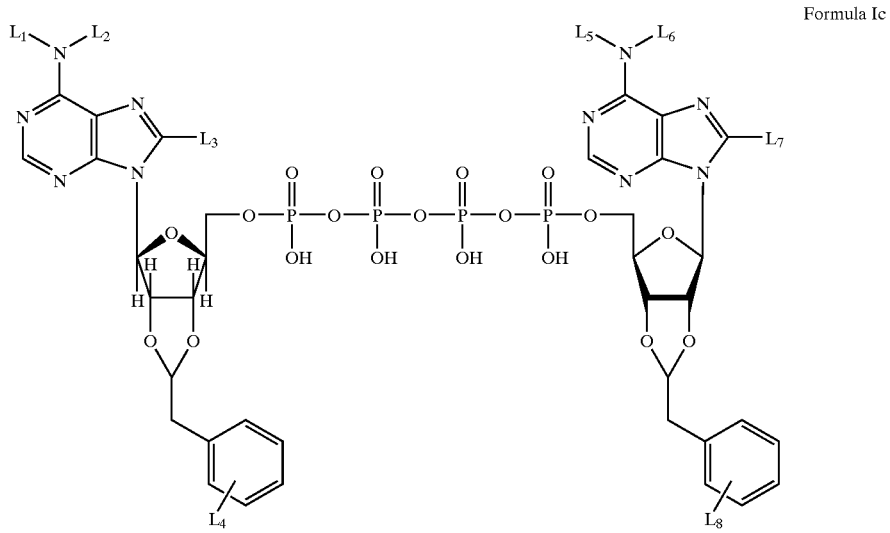

Formula Ic wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ and $L_8$ are independently selected from the group consisting of H, $C_1$–$C_6$ alkyl, aryl, $C_1$–$C_3$ alkylthio, $CF_3$, $CF_2CF_3$, —CN and —$N_3$.

16. The method according to claim 15, wherein $L_1=L_2=L_3=L_4=L_5=L_6=L_7=L_8$=H.

17. The method according to claim 1, wherein said compound is a compound of Formula Id, or a 2'-ester or ether thereof, or 3'-ester or ether thereof:

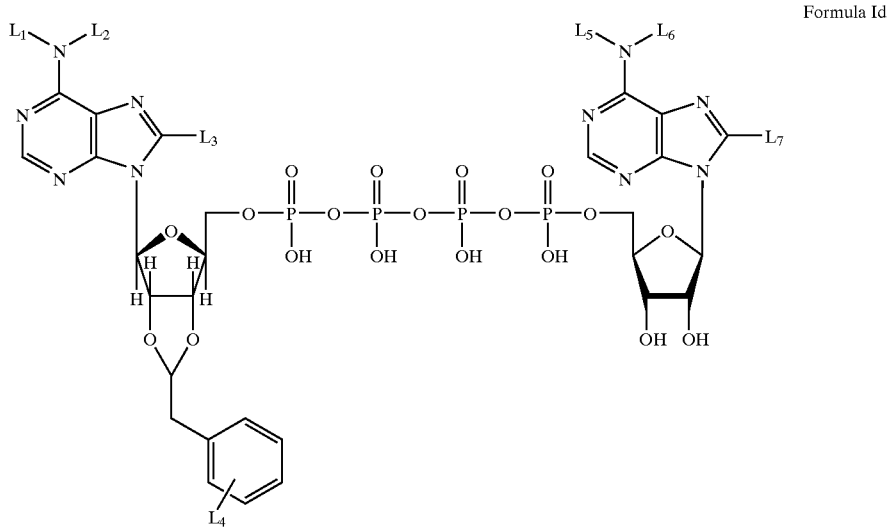

Formula Id wherein $L_1$, $L_2$, $L_5$ and $L_6$ are independently selected from the group consisting of H, $C_1$–$C_4$ alkyl, phenyl, $C_1$–$C_{12}$ acyl and benzoyl;

$L_3$ and $L_7$ are independently selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

18. The method according to claim 17, wherein $L_1=L_2=L_3=L_4=L_5=L_6=L_7=H$.

19. The method according to claim 1, wherein said compound is a compound of Formula Ie:

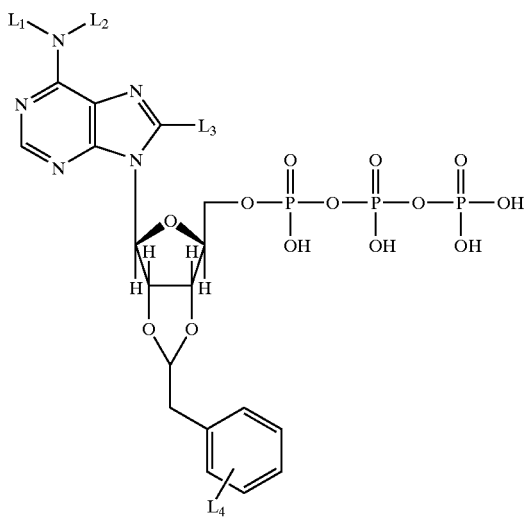

Formula Ie wherein $L_1$ and $L_2$ are independently selected from the group consisting of H, $C_1$–$C_4$ alkyl, phenyl, $C_1$–$C_{12}$ acyl and benzoyl;

$L_3$ is selected from the group consisting of H, $C_1$–$C_6$ alkyl, phenyl, $C_1$–$C_6$ alkylthio, $CF_3$, $CF_2CF_3$, and —$N_3$; and $L_4$ is selected from the group consisting of H, $C_1$–$C_6$ alkyl, aryl, $C_1$–$C_3$ alkylthio, $CF_3$, $CF_2CF_3$, —CN and —$N_3$.

20. The method according to claim 19, wherein $L_1=L_2=L_3=L_4=H$.

21. The method according to claim 1, wherein said pain is traumatic pain, neuropathic pain, organ or tissue pain, or pain associated with diseases.

22. The method according to claim 21, wherein said traumatic pain is pain resulting from injury, post surgical pain or inflammatory pain.

23. The method according to claim 21, wherein said organ or tissue pain is ocular, corneal, bone, heart, skin, visceral, joint, dental, urogenital pain, or muscle pain.

24. The method according to claim 21, wherein said diseases are cancer, AIDS, arthritis, herpes or migraine.

25. The method according to claim 1, wherein said pharmaceutical composition is administered topically to said subject.

26. The method according to claim 1, wherein said pharmaceutical composition is administered via injection to said subject.

* * * * *